(12) United States Patent
Alferness (10) Patent No.: US 8,333,715 B1
(45) Date of Patent: Dec. 18, 2012

(54) BLOOD GLUCOSE SAMPLING DEVICE

(76) Inventor: Clifton A. Alferness, Port Orchard, WA (US)

( * ) Notice: Subject to any disclaimer, the term of this patent is extended or adjusted under 35 U.S.C. 154(b) by 499 days.

(21) Appl. No.: 12/575,405

(22) Filed: Oct. 7, 2009

Related U.S. Application Data (60) Provisional application No. 61/195,352, filed on Oct. 7, 2008.

(51) Int. Cl.
- *A61B 5/00* (2006.01)
- *A61B 5/15* (2006.01)
- *A61B 5/151* (2006.01)
- *A61B 5/157* (2006.01)
- *A61B 10/02* (2006.01)
- *A61B 17/32* (2006.01)

(52) U.S. Cl. ........ 600/584; 600/575; 600/583; 606/181; 606/182; 606/183; 606/184; 606/185; 606/186

(58) Field of Classification Search .............. 600/575, 600/583, 584; 606/181–186
See application file for complete search history.

(56) References Cited

U.S. PATENT DOCUMENTS

| | | | |
|---|---|---|---|
| 6,540,675 B2 | 4/2003 | Aceti et al. | |
| 6,923,764 B2 | 8/2005 | Aceti et al. | |
| 7,004,928 B2 | 2/2006 | Aceti et al. | |
| 8,012,104 B2 * | 9/2011 | Escutia et al. | 600/583 |
| 2004/0202576 A1 | 10/2004 | Aceti et al. | |
| 2006/0094985 A1 | 5/2006 | Aceti et al. | |
| 2007/0167869 A1 * | 7/2007 | Roe | 600/583 |
| 2007/0167872 A1 * | 7/2007 | Freeman et al. | 600/583 |
| 2008/0077048 A1 | 3/2008 | Escutia et al. | |

\* cited by examiner

*Primary Examiner* — Sean Dougherty
(74) *Attorney, Agent, or Firm* — Patrick J. S. Inouye; Krista A. Wittman

(57) ABSTRACT

A blood glucose sampling device is provided. The blood glucose sampling device includes a sensor cartridge having a plurality of blades oriented in a common direction of rotation about a central point. Each blade includes a test strip having a test region defined radially from the central point at a proximal end and a capillary aligned with a distal end of the test region and extending to an outer edge of the blade. Each blade also includes a cleaning element positioned adjacent to the test strip. A lancet is affixed to a lancet cartridge and aligned with the capillary formed in the test strip. A housing removably encloses the cartridges and includes an outer grip that surrounds a circumference of the housing and is shaped to fit between a thumb and finger. A test passage formed in the outer grip through which the test strip and lancet are positioned.

12 Claims, 10 Drawing Sheets

BLOOD GLUCOSE SAMPLING DEVICE

CROSS-REFERENCE TO RELATED APPLICATION

This non-provisional patent application claims priority under 35 U.S.C. §119(e) to U.S. Provisional Patent Application Ser. No. 61/195,352, filed Oct. 7, 2008, the disclosure of which is incorporated by reference.

FIELD

This application relates in general to sampling devices and, in particular, to a blood glucose sampling device.

BACKGROUND

Diabetics, both type I and type II, who take insulin must measure the levels of their blood glucose at various times to know how much food or insulin to take to compensate for their present state. For many years, blood glucose has been measured by taking a lancing device from a pocket, purse, or testing kit, lancing through the skin of a patient's finger into the capillary bed, extracting a small drop of blood onto a test strip, and measuring the blood glucose concentration using an electronic blood glucose meter or color chart.

Specifically, to make this blood glucose measurement, a fresh test strip is first removed from a carrying case, and inserted into the blood glucose meter. A lancing device, which has a spring-loaded point tip or lancet, is then employed to prick through the skin into the patient's capillary bed, usually on a fingertip. Sometimes, particularly when the ambient temperature is cool, the finger must be "milked" or manually squeezed toward or around the lanced site to get a drop of blood that is large enough to analyze. This drop of blood is wicked into or placed on the test strip, where a chemical reaction takes place, which enables the meter to yield a measurement of the blood glucose concentration in that blood sample.

The step of getting the blood onto or into the test strip usually involves picking up the meter with a test strip already in place and moving the tip of the test strip to touch the exposed surface of the drop of blood on the pricked fingertip. The test strip usually includes a capillary or absorbent material that wicks the blood onto a glucose oxidase region, where the blood is then analyzed for blood glucose concentration.

The resultant blood glucose measurement is displayed on the meter's display screen, so that the patient can subsequently take insulin or eat food, as appropriate. Once the analysis of the blood sample is complete and the result displayed, the patient must use a tissue or similar material to remove any excess blood on the fingertip or other site from which the sample was taken. The used test strip is removed from the meter and carefully discarded. Care is taken to avoid touching the end of the strip, which still contains blood. Wiping the end of the strip with a tissue helps to remove the possibility of unwanted blood stains.

Conventionally, the taking of a blood sample for blood glucose measurement involves multiple steps, requires fresh testing supplies and equipment, specifically a lancing device and blood glucose meter. The production can take substantial time to complete for the diabetic. The supplies and equipment must be on-hand wherever the diabetic goes. Additionally, blood glucose testing is noticeable by individuals around the patient and is often an awkward or embarrassing procedure to complete in public settings due to the drawing of blood, meter usage, and clean up. Therefore, patients are often compelled to postpone the process to a more private setting so they are not embarrassed by the obtrusiveness of the process.

Attempts to improve the sampling and testing process self-performed by a patient have been made. For example, U.S. Patent Application Publication No. 2008/0077048, to Escutia et al., teaches a body fluid sampling device to automate milking of a patient digit to express a sufficient amount of body fluid. The device includes a catalyst device to apply pressure to the digit and a footprint. The digit is positioned within the catalyst, which directs blood to a sampling site on the digit, and over the footprint. The footprint guides the penetration member to the digit. However, the patient must remove his digit from the catalyst to clean up any excess blood.

U.S. Pat. No. 7,004,928 and U.S. Patent Application Publication No. 2006/0094985 to Aceti et al. teach a monitoring and drug delivery device that provides calibration and semi-continuous monitoring. The device includes a carrier having a plurality of microneedles, each coupled with a conduit, and a plurality of microchannels. One of the microneedles penetrates the skin of a patient and a blood sample is obtained, which enters the associated microchannel. After the microneedle punctures the skin, the patient must manually wipe any excess blood with a tissue.

Further, U.S. Pat. No. 6,540,675, U.S. Pat. No. 6,923,764, and U.S. Patent Application Publication No. 2004/0202576, also to Aceti et al., teach an analyte monitor having a plurality of needles each associated with a chamber configured to hold a blood sample. The sample is collected into the chamber by piercing the skin of a patient with the needle. Once collected, an arm including a detector and light source rotates to the chambers to emit a light source. An absorbance of the light is detected. Once punctured, the patient must manually clean any excess blood from the site of the pierced skin.

Therefore, a need remains for a blood glucose sampling device, which could be used by patients without having to assemble all the various supplies and equipment to accomplish the task of making a blood glucose measurement. A blood glucose sampling device that is more discrete would allow patients to make blood glucose measurements without the embarrassment of nearby people being aware that the process is taking place.

SUMMARY

A unitary sampling device impedes venous return from the blood vessels of the fingertip being tested by built-in pressure points, and impels blood toward the lancing site so that manual "milking" of the finger is not needed. The sampling device also locates the point of lancing of the fingertip whereby the resultant drop of blood is formed to touch a capillary defined on a far end of a test strip. The blood travels via the capillary to a test region covered by an enzyme electrode, including glucose oxidase and manual matching of the sensor tip to the drop of blood on the fingertip is not needed. The sampling device also includes a cleaning element for absorbing the residual blood after the completion of testing. Tissue paper is not needed to clean the lanced site.

A further embodiment provides a blood glucose sampling device. A sensor cartridge includes a plurality of blades oriented in a common direction of rotation about a central point. Each blade includes a test strip having a test region defined radially on a surface of the test strip from an outer edge of the central point at a proximal end and a capillary aligned with a distal end of the test region and extending to an outer edge of the blade. Each blade also includes a cleaning element positioned adjacent to the test strip in the common direction of rotation about the central point. The blades are positioned about the central point such that the test strip of one blade contacts the cleaning element of another blade. A lancet is affixed to a lancet cartridge and aligned with the capillary formed in the test strip. A housing removably encloses the sensor cartridge and lancet cartridge. The housing includes an outer grip surrounding a circumference of the housing and is movably shaped to conformably fit within a hand of a user between a thumb and a finger. The housing also includes a test passage formed in the outer grip through which the test strip and lancet are positioned.

A further embodiment includes a band attached to a sampling device that encircles an extremity of a patient, such as a forearm, and includes a deployable lancet to lance the skin at a preferred location on the extremity, self-locating the testing strip capillary at the lanced location, and an enclosure that creates suction that enhances the formation of a drop of blood. A mountable blood glucose sampling device is provided. The mountable blood glucose sampling device includes a sensor cartridge having a plurality of blades oriented in a common direction of rotation about a central point. Each blade includes a test strip having a test region defined radially from the central point at a proximal end and a capillary aligned with a distal end of the test region and extending to an outer edge of the blade. The sensor cartridge also includes a cleaning element positioned adjacent to the test strip in the common direction of rotation about the central point. The blades are positioned around the central point such that the test strip of one blade contacts the cleaning element of another blade. A lancet is aligned with one of the test strips. A housing is shaped to removably enclose the sensor cartridge and lancet. The housing includes a test passage formed on a back side of the housing through which the aligned test strip and lancet are positioned. A mounting band is attached to the housing and shaped to removably accommodate an extremity of a user. A suction element is affixed to the back side of the housing and formed to contact a portion of the extremity.

In yet a further embodiment, a method for constructing a blood glucose sampling device is provided. A housing sized to accommodate a lancet and a removable sensor cartridge having test strips and cleaning elements is formed. A movable outer grip is defined along a circumference of the housing and is shaped to conformably fit within a hand of a user. A test passage is formed in the outer grip in which one of the test strips and the lancet are aligned.

Such devices would encourage patients to make more frequent and timely blood glucose measurements, thereby enabling them to improve their response time to blood glucose excursions and ultimately the control or management of blood glucose.

Still other embodiments will become readily apparent to those skilled in the art from the following detailed description, wherein are described embodiments by way of illustrating the best mode contemplated. As will be realized, other and different embodiments and its several details are capable of modifications in various obvious respects, all without departing from the spirit and the scope. Accordingly, the drawings and detailed description are to be regarded as illustrative in nature and not as restrictive.

DETAILED DESCRIPTION

Figure 1:
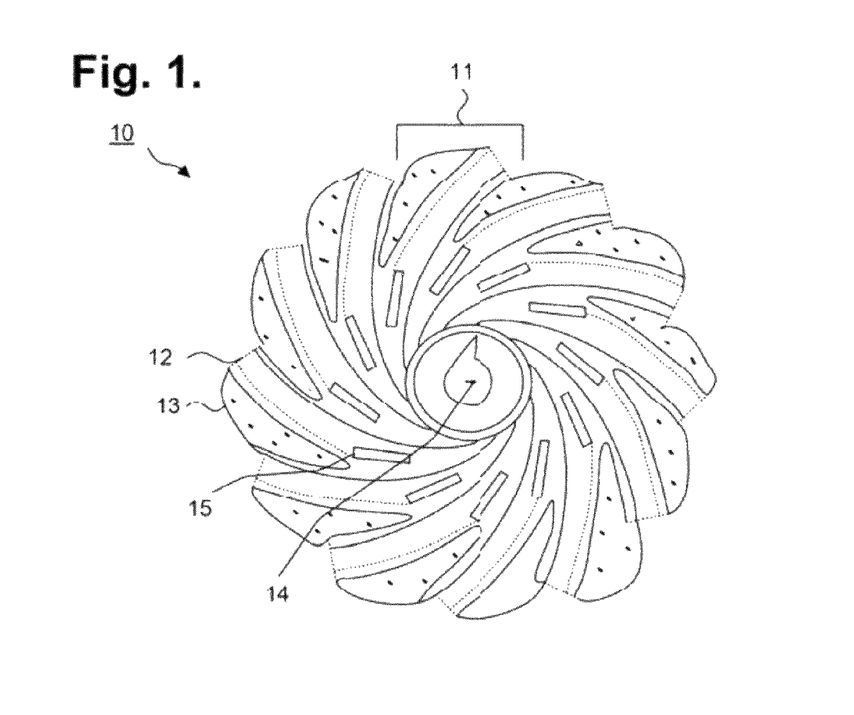
FIG. 1 is a top plan view showing a sensor cartridge for use with a blood glucose sampling device in accordance with one embodiment.

Self-monitoring of blood glucose, such as in diabetes management, can be a tedious and, at times, socially embarrassing process. A blood glucose sampling device with built-in lancing, testing, and cleaning features can allow a patient to easily and discreetly obtain blood samples and measure the sample's blood glucose level. The blood glucose sampling device includes a housing within which a lancet and a sensor cartridge are positioned. FIG. 1 is a top plan view showing a sensor cartridge 10. The sensor cartridge 10 includes a plurality of blades 11 each having a test strip 12 and a cleaning element 13. The blades 11 are oriented in a common direction of rotation around and attached at a central point 14. The test strips 12 and cleaning elements 13 are alternately positioned. For example, the test strip of one blade contacts both the corresponding cleaning element for the blade and a cleaning element of another neighboring blade.

Each test strip 12 includes an individual test region 15 having enzyme electrodes located at an inner or proximal end of the test strip 12, nearest to the central point 14. On one surface of the test strip, a capillary is defined inwardly from an outer edge or distal edge of the blade and feeds into the testing region. A lancet (not shown) impales the skin of a patient to obtain a blood sample for testing. The lancet is aligned with a capillary in a clean test strip so that the blood enters the capillary and flows to the testing region. Obtaining a sample using the lancet and test strip are further discussed below with reference to FIGS. 7A and 7B.

The cleaning element 13 is positioned adjacent to the test strip to remove and absorb the excess blood from the fingertip after the sensor capillary has wicked sufficient blood to complete testing. Excess blood is removed by manually or automatically rotating the sensor cartridge so that the cleaning element 13 is adjacent to the puncture point after completion of the blood glucose analysis. Rotation can be provided by a motor and the like. The cleaning element 13 can include an absorbent material, such as a fabric or open cell sponge material. Other types of absorbent materials are possible. The cleaning element 13 relieves the patient from the messy and socially intrusive task of wiping off the excess blood with a facial tissue or equivalent absorptive material.

The sensor cartridge includes a mount opening that is shaped to be received by a shaft rotatably provided in the device housing (not shown). The mount opening can be located at the central point of the sensor cartridge, or alternatively, at another point. The mount opening is further described below with reference to FIG. 2. In a further embodiment, the mount opening is keyed to ensure locking of the sensor cartridge 10 to the shaft.

Figure 2:
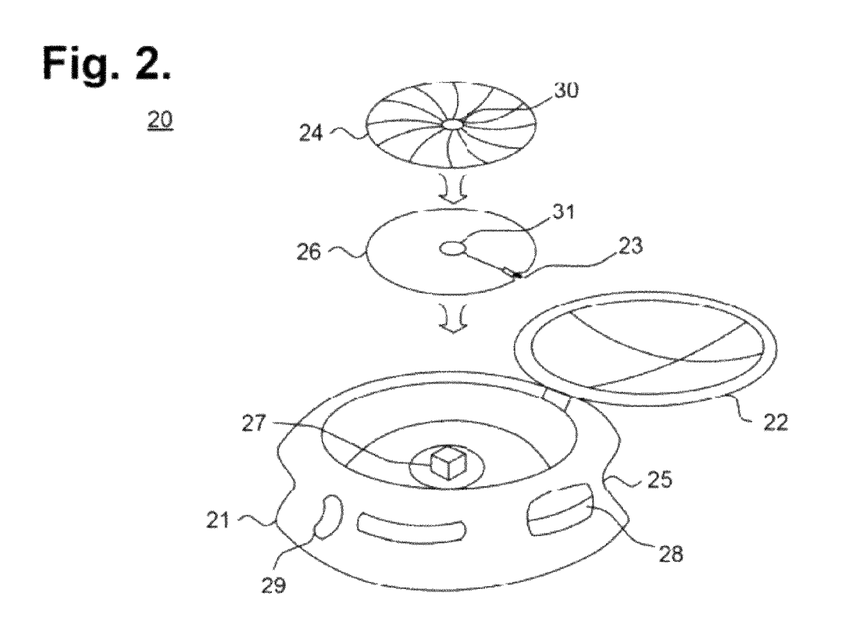
FIG. 2 is an exploded view showing a blood glucose sampling device assembly, including a housing, lancet, and the sensor cartridge of FIG. 1.

The sensor cartridge 10 can be removably enclosed with a housing. FIG. 2 is an exploded view showing a blood glucose sampling device assembly, including a housing, lancet, and the sensor cartridge of FIG. 1. The lancet 23 can be affixed to a lancet cartridge 26 in which a mount opening 31 is formed centrally or off-center. The mount opening 31 is shaped to receive a shaft positioned within the housing 21. The lancet 23 can be affixed adjacent to an outer edge of the lancet cartridge 26 to allow extension and retraction of the lancet 23. The lancet 23 is spring-loadable or otherwise slidably-oriented to facilitate lancing of the fingertip.

In a further embodiment, the lancet cartridge 26 and sensor cartridge 24 can be combined to form a single cartridge, the lancet 23 can be affixed to the sensor cartridge 24, or the lancet 23 can be affixed to the housing 21. The lancet 23 is be aligned with a test strip of the sensor cartridge 24.

In yet a further embodiment, multiple lancets can be included on the sensor cartridge, lancet layer, or affixed to the housing so that each lancet corresponds with a blade of the sensor cartridge. The patient can singly use the corresponding blade and lancet.

The housing 21 can be made of materials, including heavy plastic or metal, and is shaped to enclose the sensor cartridge 24 and lancet cartridge 23. The housing can be opened on one side, which allows placement and removal of the sensor cartridge 24 and lancet cartridge 23. The open side can be covered with a door pivotably or otherwise removably attached to the housing. One or more displays (not shown) can be affixed to the door or to another side of the housing for providing readings of the blood samples collected and analyzed by the sampling device.

The sensor cartridge 24 and lancet cartridge 23 can be removably positioned within the housing via a shaft, which forms a cartridge mount 27. Specifically, the mount openings in the sensor cartridge 24 and lancet cartridge 23 are placed over the shaft 27 and secured. The shaft 27 can be located centrally or off-center within the housing 21. When located centrally, the shaft 27 is positioned at the central point of rotation for the sensor cartridge 24. The sensor cartridge 24 can rotate within the housing 21 about the central point so that for each test, a new test strip and cleaning strip are respectively aligned in the test passage during sampling.

The outside of the housing includes an outer grip 25 that is shaped to conformably fit within a hand of a patient. Within the outer grip 25, a test passage 28 is formed to receive a finger, through which the lancet and capillary of the test strip are aligned for obtaining a sample from a patient. An opening of the test passage formed within the outer grip 25 is shaped to receive a body part of a patient, such as a finger.

A sensor cartridge actuator 29 and test actuator (not shown) can also be included in the outer grip 25. The actuators can include a pushable button, toggle, or switch, as well as other mechanisms. The sensor cartridge actuator 29 is located at a distance from the test passage 28 around the circumference of the outer grip 25. The placement of the sensor cartridge actuator 29 is further discussed below with reference to FIGS. 4-8. Upon selection, the sensor cartridge actuator 29 can advance the sensor cartridge 24 into position within the housing 21 so that the test strip of a blade is aligned with the lancet in the test passage 28. The sensor cartridge can be further advanced in the same direction so that the cleaning element of the blade is aligned in the test passage 28. The rotation of the sensor cartridge can be directed by selection of the sensor cartridge actuator. For example, in one embodiment, the test strip is aligned in the test passage upon depression of the sensor, cartridge actuator and the cleaning element is aligned upon release of the same sensor cartridge actuator. In a further embodiment, the test strip and cleaning element are aligned in the test passage using separate sensor cartridge actuators. The sensor cartridge actuator 29 can activate the display or displays affixed to the housing.

The test actuator can also be affixed to the outer grip 25 of the housing 21 substantially adjacent to the test passage 28. Upon selection of the test actuator, the lancet is cocked, released, and extended through the test passage into the test passage opening. In one example, the test actuator is a button that cocks and releases the lancet towards a patient's finger or other body part upon depression. Once extended, the lancet impales the finger that is placed over the test passage opening. Then, the lancet can be retracted upon release of the test button. In a further embodiment, the release and retraction of the lancet can be performed upon the selection of separate actuators or upon selection of the same actuator.

Depression of the test actuator requires pushing provided by a test finger of the patient. The pushing accomplishes milking of the finger, which directs and traps blood in the tip of the test finger so that the tip is engorged with blood during impalement. Deployment of the lancet into the fingertip may be performed multiple times to acquire enough blood necessary to complete a blood analysis.

Figure 3:
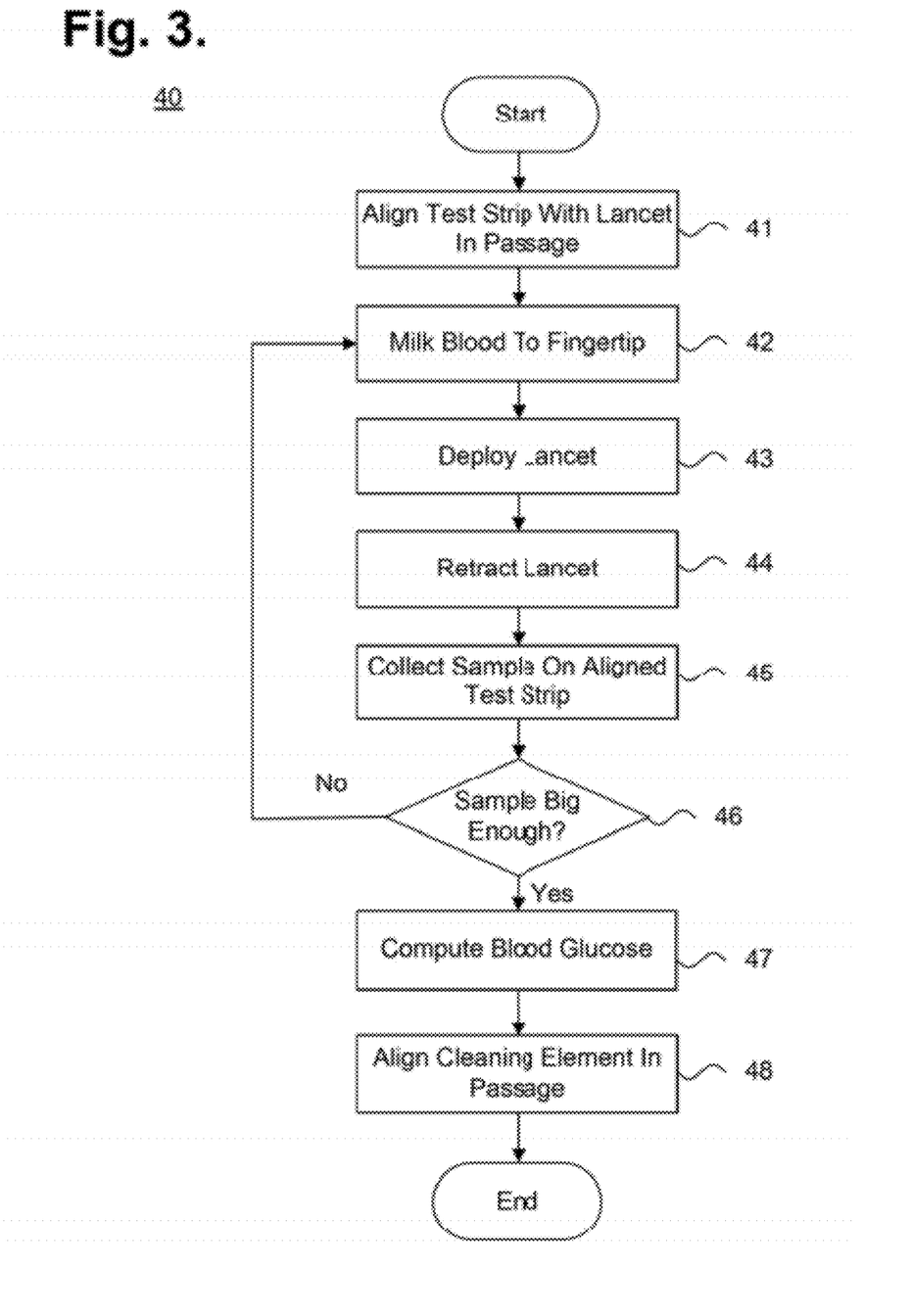
FIG. 3 is a flow diagram showing, by way of example, a process for obtaining a blood sample using the blood glucose sampling device of FIG. 2.

The blood glucose sampling device provides a simple and efficient process for obtaining and analyzing a blood sample. FIG. 3 is a flow diagram showing, by way of example, a process for obtaining a blood sample using the blood glucose sampling device of FIG. 2. The blood glucose sampling device is positioned within a patient's hand and a test finger is identified. The sampling device includes a lancet and a sensor cartridge having a plurality of blades, each including a test strip and cleaning element. Once positioned, a clean test trip within the blood glucose sampling device is aligned with the lancet in a test passage formed within the sampling device (block 41). The sampling device provides "milking" (block 42) of the test finger so that the fingertip is engorged with blood. "Milking" can occur through manual means provided by the patient, by pressure provided by the sampling device, as further described below with reference to FIGS. 5 and 6, and by suction pressure generated by the sampling device, as further described below with reference to FIG. 11.

A lancet is deployed (block 43) to pierce the skin of the engorged fingertip for obtaining a blood sample and then retracted (block 44). The blood sample is collected (block 45) on the test strip aligned with the lancet. More specifically, the sample enters a capillary formed on the test strip and travels to a test region covered with enzyme electrodes. Once collected, a determination (block 46) is made whether the sample is large enough for analysis. If not, additional sample blood must be obtained through further "milking" (block 42) of the test finger. However, if sufficiently large, the sample is analyzed to determine a blood glucose concentration. After the test finger has been pierced and the sample collected, a cleaning element is aligned (block 48) in the test passage to contact and remove any excess blood remaining. The analysis (block 47) and cleaning (block 48) can occur concurrently or sequentially.

Figure 4:
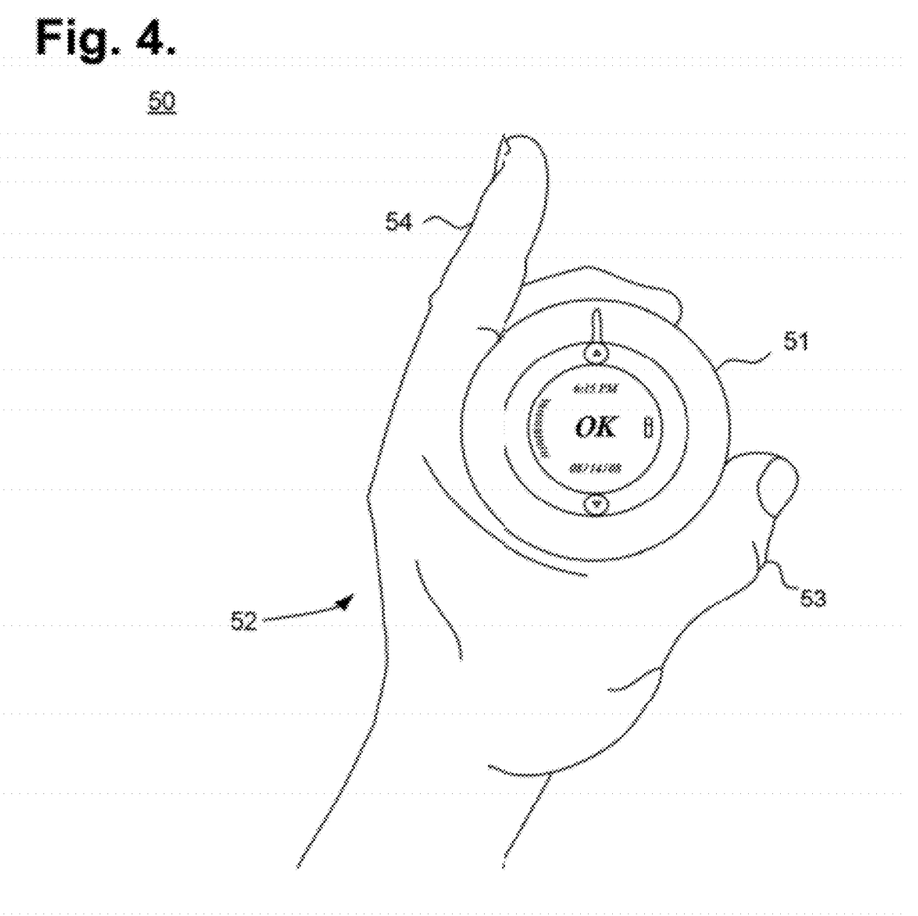
FIG. 4 is a diagram showing, by way of example, a hand holding the blood glucose sampling device of FIG. 2 with the fingers in an initial position of a sampling sequence.

FIGS. 4 through 8 show the sequence of events that occur using the sampling device for testing blood glucose. FIG. 4 is a block diagram 50 showing, by way of example, a hand 52 holding the blood glucose sampling device 51 of FIG. 2 with the fingers in an initial position of a sampling sequence. The blood glucose sampling device 51 is shaped to fit within the hand 52 of a patient, specifically between a finger 54, such as the pointer finger, and the thumb 53. Other fingers are possible. The finger 54 is selected by a patient as the test finger 54, from which a blood sample is obtained. The thumb 53 rests along the outer grip of the blood glucose sampling device on a sensor cartridge actuator (not shown), while the test finger 54 wraps around a circumference of the outer grip, towards a top of the housing. The blood glucose sampling device 51 rests along webbing of the hand 52 between the thumb 53 and pointer finger. In a further embodiment, the test finger 54 can include the thumb 53, while one of the fingers controls the sensor cartridge actuator.

Figure 5:
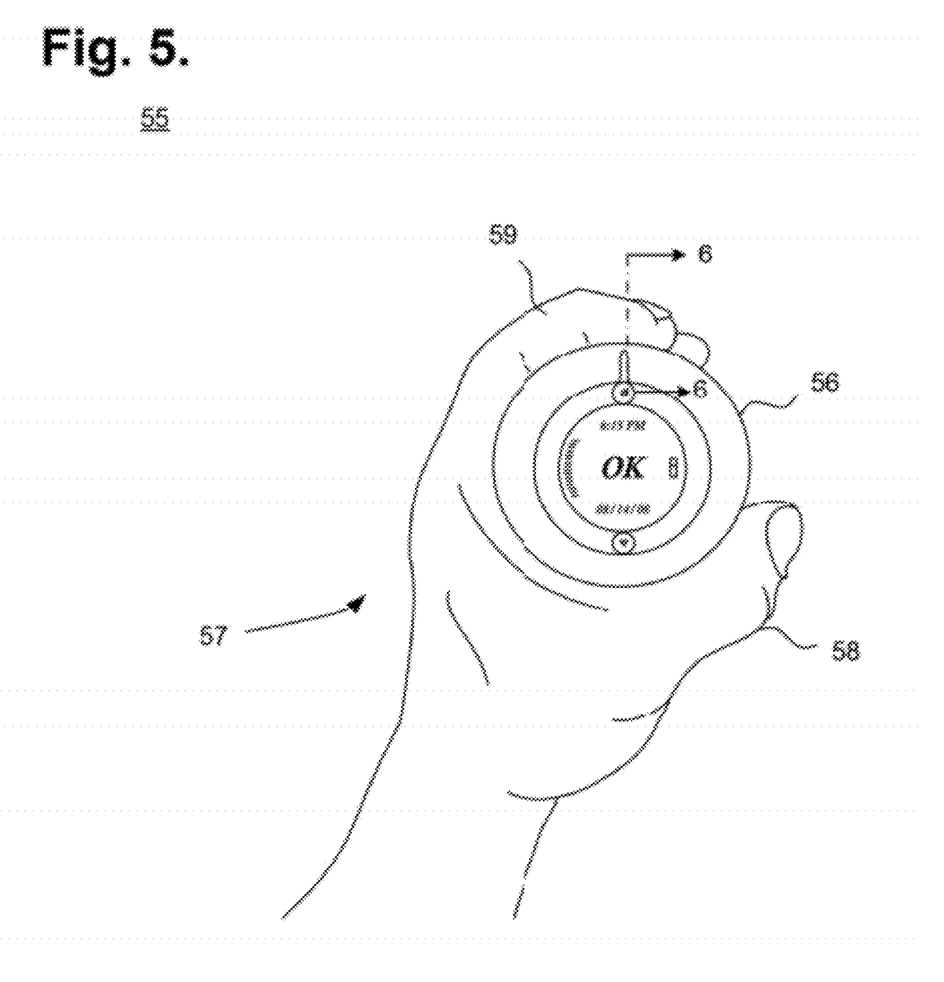
FIG. 5 is a diagram showing, by way of example, a hand holding the blood glucose sampling device of FIG. 2 with the fingers in a testing position of a sampling sequence.

FIG. 5 is a block diagram 55 showing a hand 57 holding the blood glucose sampling device 56 of FIG. 2 with the fingers 59 in a test position of a sampling sequence. The blood glucose sampling device 51 is positioned within the patient's hand 57 and a test finger 59 is sequentially wrapped around an outer grip of the device 56. The test finger 59 rests upon a test actuator (not shown) and a test passage (not shown) adjacently located in the outer grip. Meanwhile, the thumb is positioned over a sensor cartridge actuator, which rotates the sensor cartridge so that a capillary of clean test strip is aligned with a lancet in the test passage. Once the blood glucose sampling device is properly positioned within the patient's hand for testing, tissue pressure is created in the proximal portion of the test finger, nearest the palm, by the housing of the blood glucose sensor device. Due to the pressure, venous return is impeded in that the test finger while arterial blood continues to flow. This causes an engorgement of blood in the fingertip as the finger is wrapped around the blood glucose sampling device and rests upon the test actuator and test passage. An opening of the test passage formed in the outer grip allows the tip of the test finger to bulge out adjacent to the capillary of the test strip positioned within the test passage.

Figure 6:
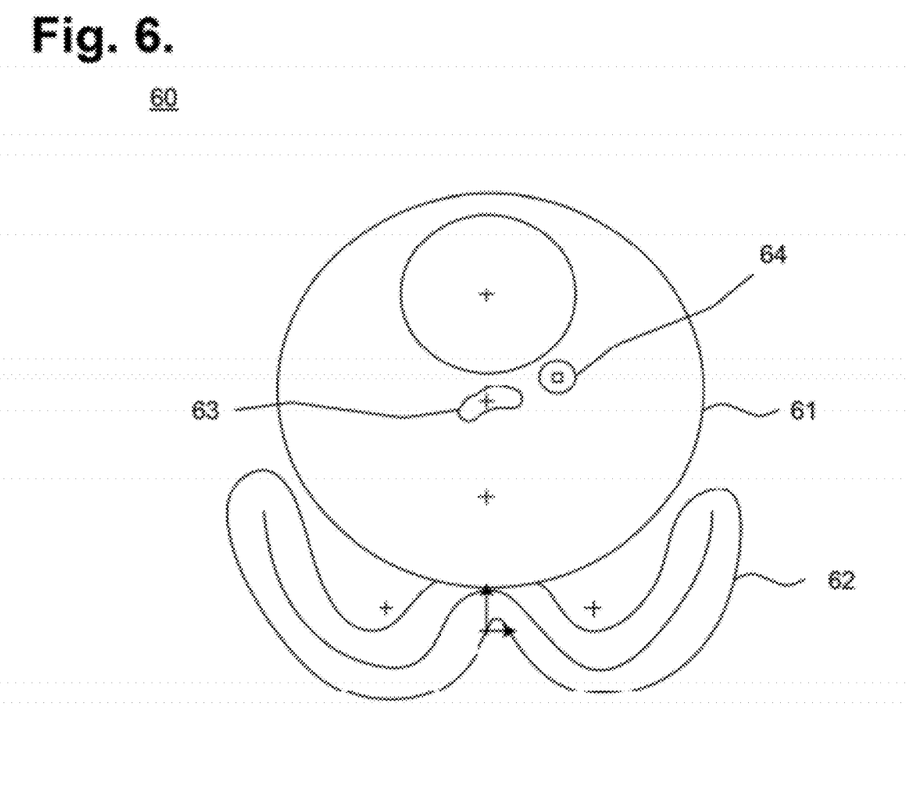
FIG. 6 is a cross-sectional view of a finger and blood glucose sampling device of FIG. 5.

The pressure is created by a protruding of the outer grip into the test finger. FIG. 6 shows a cross section of a test finger and a blood glucose sampling device of FIG. 5. The outer grip or portions of the outer grip of the housing can be made from nitinol wire and foam, which allows the outer grip to contract and expand when pressure is applied. Specifically, to impede venous return, a side of the outer grip corresponding with the proximal portion of the test finger protrudes outwards into the test finger based on a squeezing of the blood glucose sampling device sides adjacent to the protruding side. The squeezing can be performed by a distal end of the test finger, such as the fingertip, and the thumb by pressing the outer grip into the blood glucose sampling device. The increased tissue pressure within the test finger generated by the squeezing effectively prevents venous blood flow past the pressure point while allowing arterial flow. A series of such ribs accomplishes a sequential milking process.

Figure 7A:
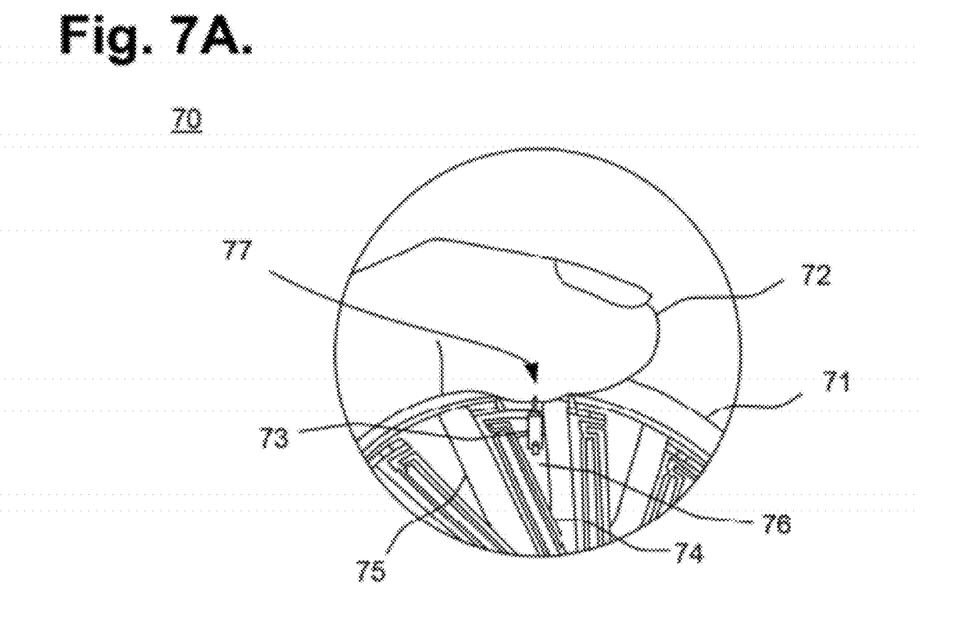
FIG. 7A is a block diagram showing, by way of example, deployment of a lancet into a finger.

Once the blood is collected in the tip of the test finger, a lancet can be deployed to obtain a sample. FIG. 7A is a block diagram 70 showing, by way of example, deployment of a lancet 73 into a test finger 72. The test finger 72 of a patient is positioned upon a test actuator (not shown) and over an opening of a test passage 76, while the thumb rests upon a sensor cartridge actuator, as described above with respect to FIG. 5. More specifically, a tip of the test finger enters the housing through the opening of the test passage. Meanwhile, the blood glucose sensing device can rest in the webbing between the thumb and pointer finger.

During testing, a new test strip should be aligned with the lancet to collect the sample. The patient can select the sensor cartridge actuator to rotate the sensor cartridge to a new test strip so that the corresponding capillary is aligned with the lancet in the test passage 76. Once aligned, the patient can squeeze the outer grip of the housing to impede venous return of the test finger, as described above with reference to FIG. 6. Thereafter, the patient can select the test actuator, which deploys the lancet to impale the skin of the engorged fingertip in precisely the correct location to form a sample blood droplet at the entrance to the capillary. The creation of fingertip engorgement or milking may be further improved by sequentially squeezing the test finger from proximal to distal using a manual mechanism.

Figure 7B:
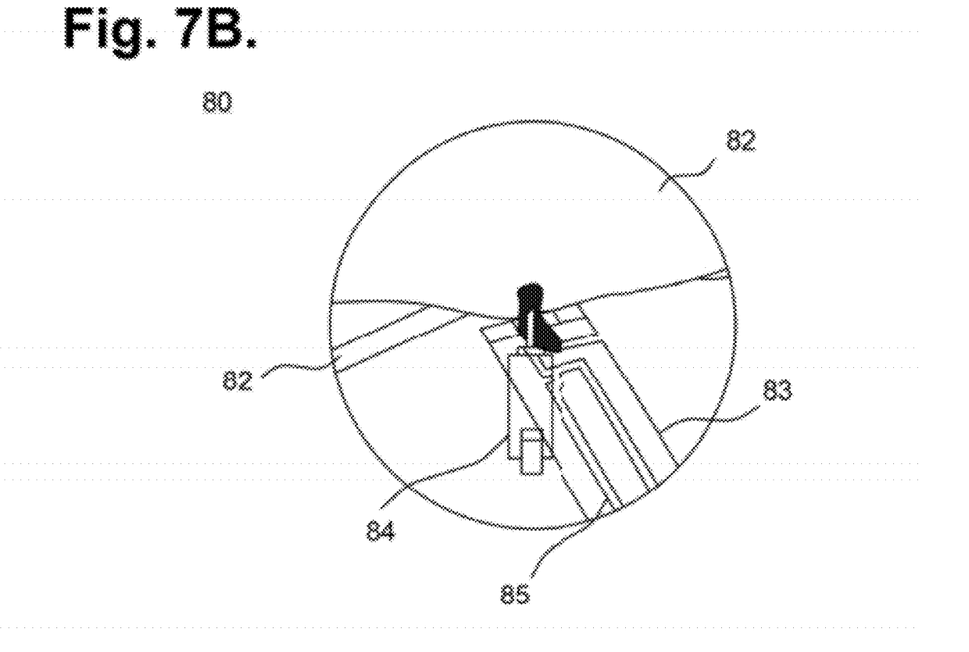
FIG. 7B is a block diagram showing, by way of example, entry of a sample into a capillary.

The blood sample is collected on the test strip aligned with the lancet. FIG. 7B is a block diagram 80 showing, by way of example, entry of a sample 85 into an blood glucose sampling device 81. A test strip 83 is aligned with a lancet 84 in the test passage. The alignment ensures that the sample obtained is located at the entrance of a capillary 85 in the test strip 83. A test finger 82 of a patient contacts the test strip 83 by entering the housing when positioned over the opening of the test passage. In a further embodiment, the test strip can extend out of the housing to ensure contact with the test finger. A sample drop of blood 85 forms on the test fingertip 82 after the lancet 84 has been removed and enters the blood glucose sampling device through a capillary 86 formed in the test strip 83. The blood 85 travels the distance of the capillary 83 to a test region (not shown) having enzyme electrodes, which analyzes the blood 85 to determine a concentration level of glucose present.

Figure 8:
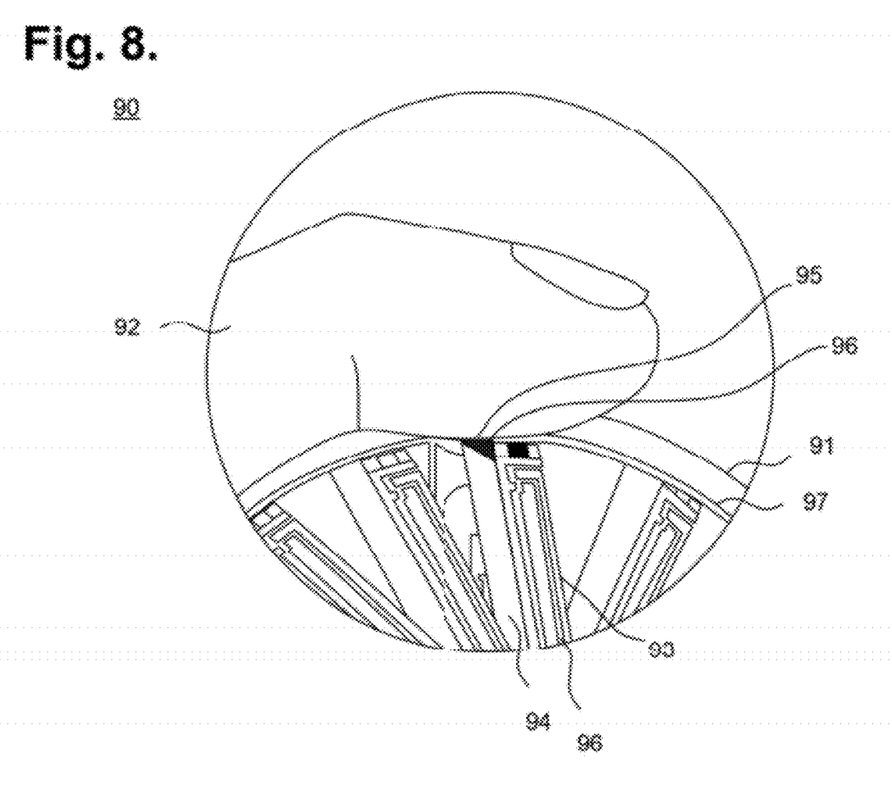
FIG. 8 is a block diagram showing, by way of example, rotation of a cleaning element to an impalement site on a finger.

Immediately after an adequate amount of blood enters the capillary, a cleaning element contacts the test finger. FIG. 8 is a block diagram 90 showing, by way of example, rotation of a cleaning element 94 to an impalement site 95 on a test finger 92. Once the sample has entered a capillary 96 formed in a test strip 93 of a blood glucose sampling device 91, a sensor cartridge 97 can rotate to align a cleaning element 94 with the impalement site 95 on the test finger 92. The cleaning element 94 can absorb any blood 96 remaining on the test finger 92 so that the test finger is clean once removed from the blood glucose sampling device. The rotation of the sensor cartridge 97 can be activated upon a release of a sensor cartridge actuator by a patient.

As described above with reference to FIG. 7A, the patient selects the sensor cartridge actuator to first rotate the sensor cartridge so that the test strip 93 is aligned with a lancet (not shown) in a test passage prior to or upon impalement. Release of the sensor cartridge actuator again rotates the sensor cartridge in the same direction as the first rotation to align the cleaning element in the test passage after impalement. Other mechanisms for rotating the cleaning element on the sensor cartridge are possible, including selecting a actuator, twisting a housing of the blood glucose sampling device, and rotating a knob.

Figure 9:
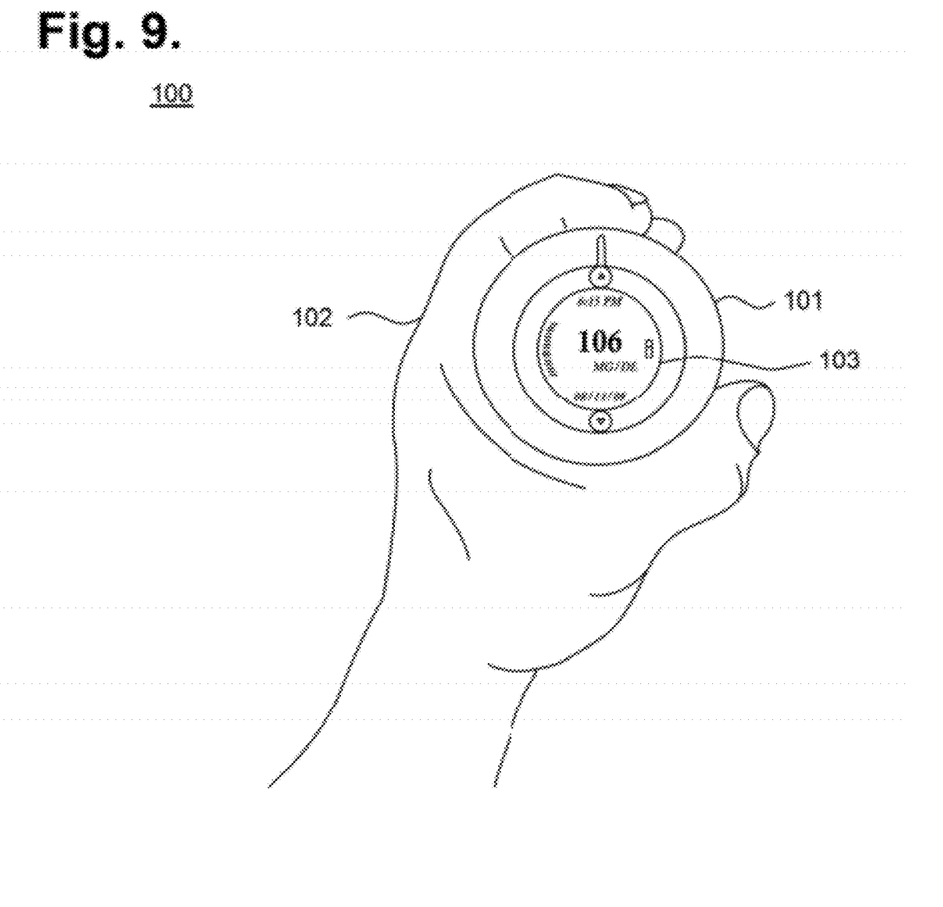
FIG. 9 is a block diagram showing a hand holding the blood glucose sampling device of FIG. 2, which displays results of a blood sample.

The obtained sample is analyzed and results are determined. FIG. 9 is a block diagram 100 showing a hand 102 holding the blood glucose sampling device 101 of FIG. 2, which displays results of a sample. The blood glucose sampling device 101 includes a display 103, which can be affixed to a front side to allow visibility by a patient holding the device 101. Other positions of the display on the blood glucose sampling device are possible. The display provides a reading of the sampling results, including a level of glucose in the patient's blood. Other information can be presented within the display, such as a time and date. The displayed results can be recorded and stored on the blood glucose sampling device, or alternatively, discarded.

Figure 10:
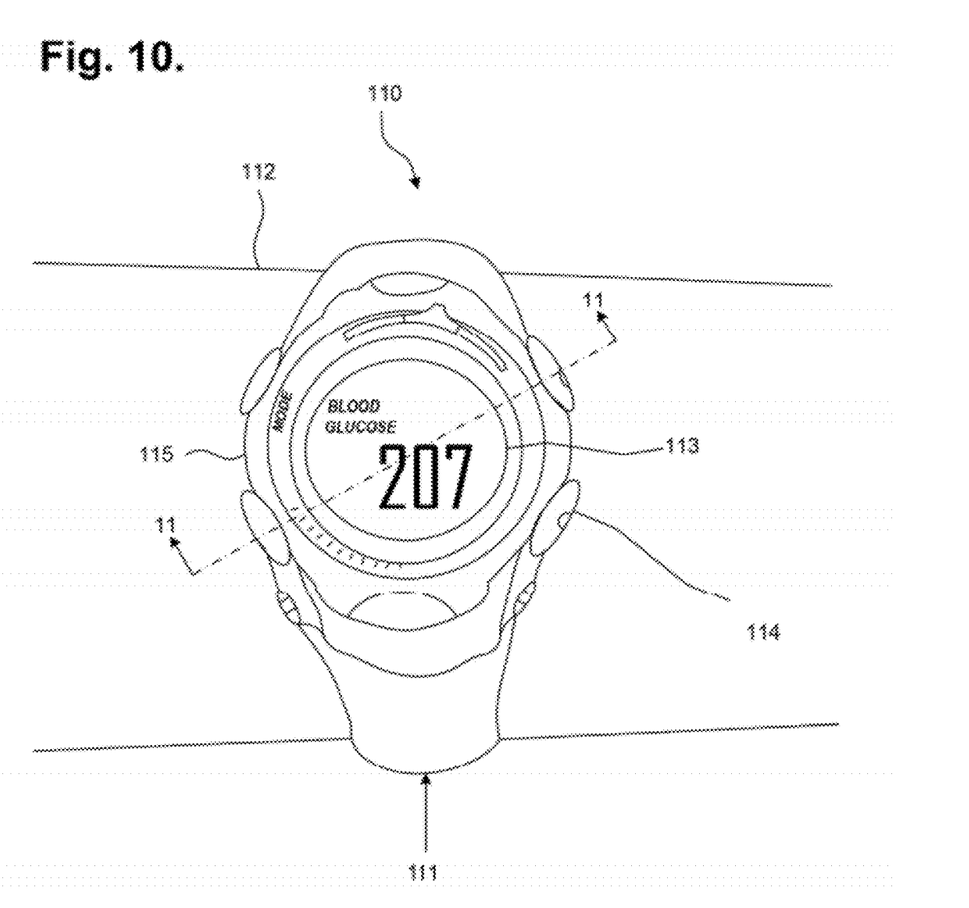
FIG. 10 is a front plan view of a mountable blood glucose sampling device.

A further embodiment includes a device mounted on a band, which is worn on an extremity of the body, such as the forearm or calf, to discreetly obtain and analyze samples, as well as to prevent loss of the device. FIG. 10 shows front view of a mountable blood glucose sampling device 110. A housing 115 of the mountable blood glucose sampling device is affixed to a mounting device 111 to removably attach to an extremity 112 of a patient. The housing 115 can be made from plastic or metal; however, other materials are possible. An example of the mounting device 111 can include a band, which wraps around the patient's extremity 112, such as a wrist or ankle. Other types of mounting devices, including a strap, belt, or cuff are possible. A front of the mountable blood glucose sampling device 110 can include a display 113 to present information. Additionally, actuators 114, such as buttons, switches, or toggles, can be positioned around a circumference of the mountable glucose sampling device 110 to initiate action performed by the device.

Figure 11:
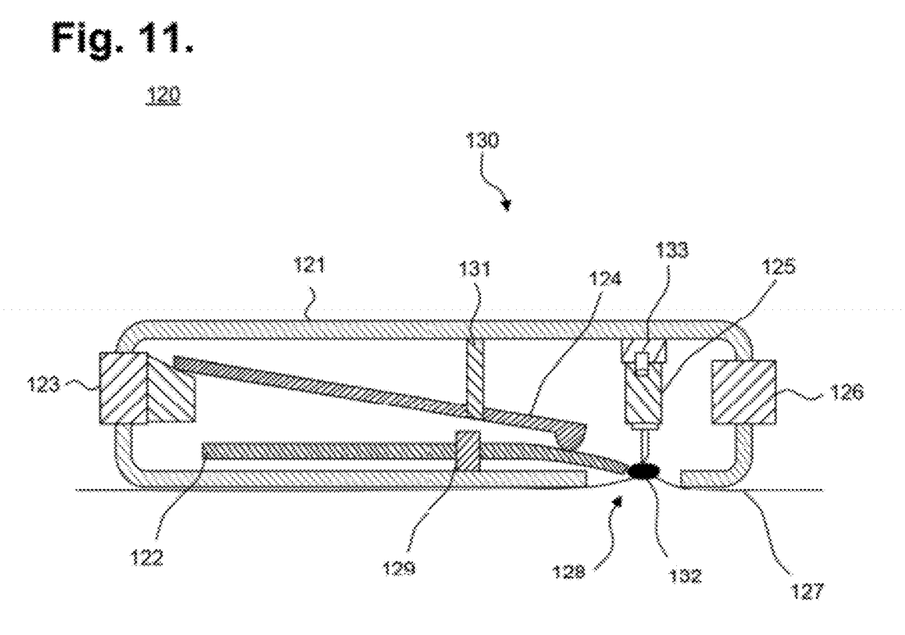
FIG. 11 is a cross-sectional view of the mountable blood glucose sampling device of FIG. 10.

The housing 115 of the mounted blood glucose sampling device 110 conformably encloses a sensor cartridge and lancet. FIG. 11 is a cross-sectional view 120 of the mountable blood glucose sampling device 130 of FIG. 10. A housing 121 of the mountable blood glucose sampling device 130 conformably encloses a sensor cartridge 122, test member 124, and lancet 125. A test passage opening 128 is formed on a back side of the mountable device 130 and positioned to contact a patient extremity 127. The test passage opening 128 provides a passage in which the lancet 125 is aligned. The sensor cartridge 122 includes a plurality of blades oriented in a common direction of rotation about a central point. Each blade includes a test strip and a cleaning element. The test strip includes a test region with enzyme electrodes that is defined radially from the central point at a proximal end. A capillary is defined inwardly from an outer edge of the test strip and terminates at a distal end of the test region. The cleaning element is positioned adjacent to the test strip in the common direction of rotation about the central point. The blades are positioned so that the test strip of one blade contacts the cleaning element of another blade.

The sensor cartridge 122 also includes a mount opening that is formed at the central point or off-center. The mount opening is shaped to receive a shaft 129 affixed to an inside of the housing 121. Once positioned, the sensor cartridge 122 can rotatably move to align an outer tip of a clean test strip over the test passage opening 128 for obtaining a blood sample 132 and to align an unused cleaning element over the test passage opening 128 for removing any excess blood. The test member 124 is pivotally positioned above the test strip or cleaning element aligned over the test passage opening 128 and can include a lever. The test member 124 is attached to the housing 121 via a pivotable attachment mechanism 131, which can include a fulcrum. In a rest position, the test member 124 is substantially parallel to the aligned test strip or cleaning element. When selected via an actuator, a proximal end of the test member pivots down toward a tip of the aligned test strip or cleaning element, and exert pressure on the tip so that contact is made with the sample 132 once obtained via the lancet 125. The lancet 125 can be directly affixed to the housing 121 via a bolt, joint or lock, or attached to a mount 133 that is affixed to the housing 121. Other means and fasteners for affixing the lancet 135 to the housing 121 are possible. The lancet 125 is located along the test passage at a substantially perpendicular angle to the sensor cartridge 122 so that an outer edge of the blades in the sensor cartridge 122 can contact the lancet 125. Other angles are possible. The lancet 125 is spring-loadable or otherwise slidably-oriented to facilitate lancing of the extremity 127 through the test passage opening 128.

The mountable blood glucose sampling device 130 also includes a suction mechanism (not shown) for creating a suction with a test site identified on the patient's extremity. The suction mechanism can be located within the housing or can be affixed to the back side of the housing. An internal suction mechanism can include a pump, and an external suction mechanism can include a suction cup. Other types of suction mechanisms are possible. The suction can aid in the formation of a blood sample on the skin surface of the test site. In one embodiment, a pushing force on the mountable blood glucose sampling device 130 can cause air to be expelled around the perimeter of the skin, which creates a seal. The suction is then created by the recoil force of a spring within the mountable blood glucose sampling device 130 to pull the skin of the extremity towards the test passage opening 128. The suction provides "milking" so that the extremity is engorged with blood and prepared for impalement by the lancet 125, which is deployed to pierce the skin of the engorged test site and retracted.

Upon lancing the skin, a blood sample is obtained. The sample enters the capillary of the clean test strip aligned over the test passage opening 128 and travels to the test region for analysis. A determination is made whether the sample is large enough for analysis. If not, additional blood must be obtained through further "milking" of the test site. However, if sufficiently large, the sample is analyzed to determine a blood glucose concentration. After the sample is collected, the sensor cartridge is rotated so the unused cleaning element is positioned over the test passage opening 128 to remove any excess blood remaining on the patient's extremity. The analysis and cleaning can occur concurrently or sequentially.

The above-identified actions can be initiated by actuators 123, 126 formed within an outer circumference of the automated sampling device housing 121. The actuators 123, 126 can include a cartridge select, lancet deploy, lancet cock, suction, and mode select actuators. The actuators 123, 126 can include a pushable button, toggle, or switch, as well as other mechanisms. Selection of the actuators 123, 126 initiates a specific action performed by the mountable blood glucose sampling device 130.

In one example, the actuators 123, 126 are pushable buttons. The cartridge select button can initiate rotation of the sensor cartridge 122 upon depression so that the capillaries of the test strip are positioned over the test passage opening 128, adjacent to the lancet 125, while release initiates further rotation of the sensor cartridge 122 to position a tip of the cleaning element over the test passage opening 128. In a further embodiment, rotation of the sensor cartridge 122 can be performed by multiple buttons or actuators. The test button can initiate movement of the test member for applying pressure on the test strip or cleaning element positioned over the test passage 128. The test member 124 can be moved via mechanical means or electrical means, which are initiated by the test pressure button. In one embodiment, the test pressure button is depressed inward, which applies an upward pressure on a distal end of the test member 124 to pivot a proximal end, nearest the lancet, down toward the tip of the test strip or cleaning element. When fully pivoted, the proximal end of the test member exerts a downward pressure on the test strip to the initiate contact with the lancet 125 or on the cleaning element to initiate contact with the sample 132.

The lancet cock button can be selected to cock the lancet for deploying into the skin of the extremity, while the lancet deploy button can deploy the lancet to impale the test site and subsequently, retract the lancet. The suction button can generate pressure necessary to create a suction between the mountable blood glucose sampling device 130 and the skin of the extremity 137. The mode button allows a patient to switch functioning and displays provided by the mountable blood glucose sampling device 130. For example, the mountable device 130 can also provide a time, date, and temperature. Other device functions, actuators, and actuator functions are possible.

While the invention has been particularly shown and described as referenced to the embodiments thereof, those skilled in the art will understand that the foregoing and other changes in form and detail may be made therein without departing from the spirit and scope.

What is claimed is:

1. A blood glucose sampling device, comprising:
    a sensor cartridge comprising a plurality of blades oriented in a common direction of rotation about a central point, each blade comprising:
        a test strip comprising a test region defined radially on a surface of the test strip from an outer edge of the central point at a proximal end and further comprising a capillary aligned with a distal end of the test region and extending to an outer edge of the blade; and
        a cleaning element positioned adjacent to the test strip in the common direction of rotation about the central point,
        wherein the blades are positioned around the central point such that the test strip of one blade contacts the cleaning element of another blade;
    a lancet affixed to a lancet cartridge and aligned with the capillary of the test strip; and
    a housing removably enclosing the sensor cartridge and lancet cartridge, comprising:
        an outer grip surrounding a circumference of the housing and movably shaped to conformably fit within a hand of a user between a thumb and a finger; and
        a test passage formed in the outer grip through which the test strip and lancet are positioned.

2. A blood glucose sampling device according to claim 1, further comprising at least one of:
    a cover pivotably attached to a substantially open side of the housing; and
    one or more displays affixed to at least one of the housing and the cover.

3. A blood glucose sampling device according to claim 1, further comprising:
    a test actuator located on the housing, wherein depression of the test actuator advances the test strip of the sensor cartridge into alignment with the lancet in the test passage and further wherein release of the test actuator advances the sensor cartridge in a common direction to align the cleaning element in the test passage.

4. A blood glucose sampling device according to claim 1, wherein the test passage is shaped to receive the finger from the hand of the user.

5. A blood glucose sampling device according to claim 1, further comprising:
    a shaft provided within the housing and shaped to rotatably accommodate the sensor cartridge and the lancet cartridge via an opening.

6. A blood glucose sampling device according to claim 1, wherein the outer grip comprises at least one of nitinol wire and foam, and further wherein the outer grip impedes venous return in the finger of the user.

7. A mountable blood glucose sampling device, comprising:
    a sensor cartridge comprising a plurality of blades oriented in a common direction of rotation about a central point, each blade comprising:
        a test strip having a test region defined radially from the central point at a proximal end and a capillary aligned with a distal end of the test region and extending to an outer edge of the blade; and
        a cleaning element positioned adjacent to the test strip in the common direction of rotation about the central point,
        wherein the blades are positioned around the central point such that the test strip of one blade contacts the cleaning element of another blade;
    a housing shaped to removably enclose the sensor cartridge and comprising a test passage opening formed on a back side of the housing;
    a lancet affixed to an inside of the housing and slidably aligned at the test passage opening;
    a test member pivotably affixed to the inside of the housing and positioned substantially parallel to and above one of the blades that is located over the test passage opening;
    a mounting band attached to the housing and shaped to removably accommodate an extremity of a user; and
    a suction element affixed to the back side of the housing and formed to facilitate contact between a portion of the extremity and the test passage opening.

8. A mountable blood glucose sampling device according to claim 7, further comprising at least one of:
    a cover pivotably attached to a substantially open side of the housing; and
    one or more displays affixed to at least one of the housing and the cover.

9. A mountable blood glucose sampling device according to claim 7, further comprising:
    a plurality of buttons comprising at least one of a test button, a mode select button, a sensor select button, a lancet deploy button, a lancet retract button, and a suction button installed on the housing.

10. A mountable blood glucose sampling device according to claim 7, wherein the test element extends down toward a tip of the blade aligned over the test passage opening and extends a downward pressure on the tip.

11. A mountable blood glucose sampling device according to claim 7, wherein the sensor cartridge rotates within the housing to align a tip of at least one of the test strip and the cleaning element over the test passage opening.

12. A mountable blood glucose sampling device according to claim 7, further comprising:
    a shaft provided within the housing and shaped to rotatably accommodate the sensor cartridge via the opening.

* * * * *